United States Patent [19]

Brenner

[11] 4,157,352

[45] Jun. 5, 1979

[54] PROCESS FOR THE MANUFACTURE OF A CYCLOPENTENEDIONE

[75] Inventor: Wolf Brenner, Füllinsdorf, Switzerland

[73] Assignee: Hoffmann-La Roche Inc., Nutley, N.J.

[21] Appl. No.: 926,593

[22] Filed: Jul. 19, 1978

[30] Foreign Application Priority Data

Aug. 12, 1977 [CH] Switzerland .......................... 9910/77

[51] Int. Cl.² ............................................. C07C 45/00
[52] U.S. Cl. ........................................... 260/586 P
[58] Field of Search ........................ 260/586 P, 586 R

[56] References Cited

PUBLICATIONS

Stetter et al., "Chem. Ber.", 100: pp. 2837–2841, (1967).
Russell et al., "J.A.C.S." 1974, 96:23, pp. 7249–7253, (1974).

Primary Examiner—Norman Morgenstern
Attorney, Agent, or Firm—Jon S. Saxe; Bernard S. Leon; William H. Epstein

[57] ABSTRACT

A process for the manufacture of 2,2,4-trimethyl-cyclopent-4-ene-1,3-dione by oxidizing 3,5,5-trimethyl-cyclohex-2-ene-1,4-dione with oxygen or an oxygen-containing gas in the present of a manganese, cobalt or copper containing catalyst.

17 Claims, No Drawings

PROCESS FOR THE MANUFACTURE OF A CYCLOPENTENEDIONE

BACKGROUND OF THE INVENTION

The cyclopentenedione, 2,2,4-trimethyl-cyclopent-4-ene-1,3-dione is a known compound having olfactory properties and useful as an intermediate in various systems. Hitherto, the aforementioned cyclopentenedione was accessible only in a complicated manner, for example via 3,3-dimethyl-bicyclo [3.1.0.] hexanedione (2,4), and in low yields.

SUMMARY OF THE INVENTION

The process of the invention, provides the said cyclopentenedione in high yields. This process comprises oxidising 3,5,5-trimethyl-cyclohex-2-ene-1, 4-dione with oxygen or an oxygen-containing gas in the presence of manganese, cobalt or copper catalyst.

DETAILED DESCRIPTION

In accordance with this invention, any manganese, cobalt or copper containing compound can be utilized as a catalyst in carrying out the process of this invention. Among the manganese, copper, and cobalt containing compounds which can be utilized in the process of this invention include salts of manganese, cobalt and copper. Among these salts are included salts of organic and inorganic acids, as well as salts of an enol.

As the catalyst there is conveniently used a salt of manganese, cobalt or copper with a weak acid, for example a lower alkanecarboxylic acid containing from 1 to 7 carbon atoms such as formic acid, acetic acid or propionic acid.

In accordance with another preferred embodiment of the process provided by the present invention there is used as the catalyst a manganese, cobalt or copper salt of an enol, for example an acetylacetonate of these metals.

An especially preferred embodiment consists in using manganese acetate or manganese acetylacetonate as the catalyst.

If desired, the reaction can be advantageously carried out by oxidation in the presence of pyridine or a homologue of pyridine, namely a lower alkyl-substituted pyridine such as collidine, picoline, lutidine or 2-methyl-5-ethyl-pyridine.

The oxidation is conveniently carried out in an inert organic solvent which at least partially dissolves the catalyst. Any conventional organic solvent in which the catalyst is partially soluble can be utilized. Examples of such solvents are aromatic hydrocarbons such as benzene, toluene or xylene, ethers, especially di(lower alkyl) ethers such as diethyl ether, or pyridine or a lower alkyl-substituted pyridine, whereby in the latter case this solvent simultaneously takes on the function of a co-catalyst.

The oxidation can be carried out conveniently at a temperature range from about 40° C. to about 110° C., especially between about 55° C. and about 70° C. A quite especially preferred temperature range lies between 55° C. and 65° C.

The oxidation can be carried out with oxygen or an oxygen-containing gas. When air is used as the oxygen-containing gas, the oxidation proceeds about half as quickly as when pure oxygen is used.

The term lower alkyl designates both branched chain and straight chain alkyl groups containing from 1 to 7 carbon atoms such as methyl, ethyl, propyl, etc.

The following Example illustrates the present invention:

EXAMPLE 220.5 g of manganese (II) acetate tetrahydrate are dissolved in 1800 ml of pyridine in a 4 liter flask provided with a stirrer, reflux condenser, gas-inlet tube and thermometer. 1368 g of ketoisophorone are added at 60° C. while gassing with oxygen and stirring untensively. 3–4 minutes thereafter a weak exothermic reaction takes place. Simultaneously, the mixture slowly takes up oxygen.

After a period of 20 hours, about 73% of the ketoisophorone have reacted. The mixture is re-condensed (boiling point: 30°–180° C./0.1 mmHg.

Condensate=2937.5 g

Residue—143.8 g (after removal of the catalyst)

The condensate is fractionated on a 1.5 m column containing Fenske ring packing.

There are obtained 602 g of 2,2,4-trimethyl-cyclopent-4-ene-1,3-dione.

I claim:

1. A process for the manufacture of 2,2,4-trimethyl-cyclopent-4-ene-1,3-dione, which comprises oxidizing 3,5,5-trimethyl-cyclohex-2-ene-1,4-dione with oxygen or an oxygen-containing gas in the presence of a catalyst selected from the group consisting of manganese, cobalt or copper containing compounds.

2. The process of claim 1, wherein the catalyst is a salt of manganese, cobalt or copper with a weak acid.

3. The process of claim 2, wherein said weak acid is a lower alkanecarboxylic acid.

4. The process of claim 3, wherein said lower alkanecarboxylic acid is formic acid, acetic acid or propionic acid.

5. The process of claim 4, wherein manganese acetate is the catalyst.

6. The process of claim 1, wherein a manganese, cobalt or copper salt of an enol is the catalyst.

7. The process of claim 6, wherein said enol is an acetylacetonate.

8. The process of claim 7, wherein manganese acetylacetonate is the catalyst.

9. The process of claim 1 wherein the oxidation is carried out in the presence of pyridine or a lower alkyl-substituted pyridine.

10. The process of claim 9, wherein said lower alkyl-substituted pyridine is collidine, picoline or lutidine.

11. The process of claim 1, wherein the oxidation is carried out in an inert organic solvent in which the catalyst is at least partially soluble.

12. The process of claim 11, wherein an aromatic hydrocarbon, an ether or pyridine or a lower alkyl-substituted pyridine is used as the solvent.

13. The process of claim 12, wherein said aromatic hydrocarbon is benzene, toluene or xylene.

14. The process of claim 12, wherein said ether is a di(lower alkyl) ether.

15. The process of claim 14, wherein said di-(lower alkyl) ether is diethyl ether.

16. The process of claim 1, wherein the oxidation is carried out at a temperature of from about 40° C. to 110° C.

17. The process of claim 16, wherein the oxidation is carried out at a temperature of from 55° C. to 70° C.

* * * * *